United States Patent [19]

Genna et al.

[11] 4,228,515

[45] Oct. 14, 1980

[54] METHOD AND APPARATUS OF DIGITAL CALIBRATION AND POSITION ANALYSIS OF A RADIANT EMISSION

[76] Inventors: Sebastian Genna, 618 Belmont St., Watertown, Mass. 02172; Sing C. Pang, 2 Soldier's Field Pk., Apt. #601, Boston, Mass. 02160

[21] Appl. No.: 915,286

[22] Filed: Jun. 13, 1978

Related U.S. Application Data

[63] Continuation-in-part of Ser. No. 677,205, Apr. 15, 1976, Pat. No. 4,095,107.

[51] Int. Cl.³ .............................................. G01T 1/20
[52] U.S. Cl. ................................. 364/571; 250/363 S; 250/366; 364/414; 364/527
[58] Field of Search ............ 364/571, 414, 527, 579, 364/570, 559, 560; 250/363 S, 445 T, 366

[56] References Cited

U.S. PATENT DOCUMENTS

| | | | |
|---|---|---|---|
| 4,074,135 | 2/1978 | Stevens | 250/366 |
| 4,075,483 | 2/1978 | Tancrell et al. | 250/366 X |
| 4,095,107 | 6/1978 | Genna et al. | 250/363 S |
| 4,151,416 | 4/1979 | Richey et al. | 250/363 S |

*Primary Examiner*—Edward J. Wise
*Attorney, Agent, or Firm*—Joseph S. Iandiorio

[57] ABSTRACT

Digital calibration and position analysis of impingement of a radiant emission on a multi-cell detector for calibration, including: directing radiant emissions to the multi-cell detector from a number of known origin positions and for each radiant emission from each origin position sampling the response of each cell, converting from analog to digital form the amplitude response of each cell; normalizing the digitized amplitude response of each cell; averaging the normalized digital amplitude response of each cell; determining from the average normalized digitized amplitude response and normalized digitized amplitude responses of each cell, the standard deviation value for each cell and the slope of the amplitude response of each cell; determining from the ratio of the slope and deviation values a weighting factor for the uncertainty of response of each cell at each origin position; determining with respect to each cell whether the origin position is to the left or right of that cell; and storing in one of a right and a left table for each cell a function of each origin position of emission, weighting factor, and normalized amplitude response for each cell for each origin position.

11 Claims, 17 Drawing Figures

POSITION ANALYSIS TABLES
TUBE $C_2$ (CENTERED AT $x$ = 1 UNIT)

| H | LEFT TABLE | | | RIGHT TABLE | | |
|---|---|---|---|---|---|---|
| | $x$ | S | $\omega$ | $x$ | S | $\omega$ |
| 0.55 | 1.78 | 12.75 | 7.16 | 2.17 | 16.43 | 7.57 |
| 0.50 | 1.66 | 21.36 | 12.87 | 2.30 | 31.28 | 13.60 |
| 0.45 | 1.56 | 26.32 | 16.87 | 2.40 | 44.66 | 18.61 |
| 0.40 | 1.47 | 26.83 | 18.25 | 2.46 | 51.93 | 21.11 |
| 0.35 | 1.38 | 23.16 | 16.78 | 2.54 | 57.00 | 22.44 |
| 0.30 | 1.24 | 13.78 | 11.11 | 2.63 | 57.05 | 21.69 |

METHOD AND APPARATUS OF DIGITAL CALIBRATION AND POSITION ANALYSIS OF A RADIANT EMISSION

RELATED CASE

This application is a Continuation-In-Part of application Ser. No. 677,205, filed Apr. 15, 1976, Sebastian Genna and Sing Chin Pang, entitled TRANSAXIAL RADIONUCLIDE EMISSION CAMERA APPARATUS AND METHOD, now U.S. Pat. No. 4,095,107.

FIELD OF THE INVENTION

This invention relates to a method and apparatus for digital calibration and position analysis of impingement of a radiant emission on a multicell detector, and more particularly to such for use with a radionuclide emission camera.

BACKGROUND OF INVENTION

A nuclear medicine diagnostic method images radiopharmaceutical distributions using a scintillation camera. A radio-pharmaceutical, a compound containing a gamma ray-emitting redionuclide, is administered to a patient and concentrates in tissues to be diagnosed. A scintillation camera is used to subsequently detect gamma ray emission to analyze the trajectory so that one or two-dimensional projected images of the radionuclide distributions may be constructed. The scintillation camera may be the type disclosed in U.S. Pat. No. 3,011,057. In this type of patent, the detector is a planar sodium-iodide scintillation crystal coupled through one or more light pipes to a one or two-dimensional array of closely packed photomultipliers. The light from the scintillation event is distributed to the photomultipliers both directly and as a result of reflection within the scintillator and light pipe. The scintillation crystal converts the gamma rays to light, to which the photomultipliers are responsive. The photomultipliers convert the collected light into an electronic pulse, the charge of which is proportional to the quantity of light received and thus, too, to the energy of the gamma ray received.

Recently, cameras having arcuate, one-dimensional, and cylindrical, two-dimensional, geometries, have been suggested by the applicants herein, Genna and Pang, in the parent application. Such cameras are particularly well suited for use in the reconstruction of transaxial emission images from gamma ray projections, using emission computerized axial tomography.

The determination of the position of a scintillation event, position analysis, from the partition of light to photomultipliers, presents formidable non-linearity and non-isotropicity problems which are not satisfactorily solved by known analog techniques. These problems generally manifest themselves as degraded energy and position resolution, image distortions, and non-uniformity. The problems are compounded when the camera uses unusual detector geometries, such as arcuate and cylindrical. The analog methods are generally based on a linear analysis of a system in which the partition of light is non-linear. That is, the response of a photomultiplier or a group of photomultipliers in a scintillation camera is not a linear function of the displacement of the scintillation event from the photomultiplier axes. Non-isotropicity derives from the inherent non-isotropic crystal and photomultiplier response, non-uniform crystal and light pipe boundary reflectivity conditions, non-uniform optical couplings, and end effects. Prior art techniques attempt to improve linearity by manipulating the light collection geometry and the photomultiplier signals prior to the position analysis. For example, in the above identified U.S. patent the planar photomultiplier surface is a substantial distance from sources of scintillation in order to improve linearity. In U.S. Pat. No. 3,919,556, attempts to improve linearity include use of spherically shaped photomultiplier windows. Other well-known techinques include light pipe shaping; light masking of the interfaces between the light pipe and the photomultiplier windows; selective light absorption at external surfaces such as crystal edges and light pipe surfaces between photomultiplier windows; and non-linear electronics, such as threshold amplifiers. However, these techniques exchange improved linearity for diminished and poorer photon statistics, which ultimately manifest as degradation of energy and position resolution, as well as non-uniformity. Typically the uniformity of prior art in analog position analysis devices varies by as much as plus or minus 15% over the aperture of the collimator.

SUMMARY OF INVENTION

It is an object of this invention to provide an improved method and apparatus for radiant emission position analysis.

It is a further object of this invention to provide such a method and apparatus which functions independently of the non-linearity and non-isotropicity of the camera portion.

It is a further object of this invention to provide such a method and apparatus which has improved distortion-free performance, uniformity and energy and spatial resolution.

It is a further object of this invention to provide such method and apparatus which utilizes digital calibration and position analysis to determine radiant emission trajectories.

The invention results from the realization that the accuracy of radiant emission detection techniques can be substantially increased using digital calibration and position analysis.

The invention features a method of digital calibration and analysis of the position of impingement of a radiant emission, origin position, on a scintillator which is coupled to an array of photo cells, herein referred to as a multi-cell detector. In the calibration mode, radiant emissions are directed to known origin positions on the multi-cell detector. For each origin position there are samples of the amplitude response of each cell. That amplitude response for each cell is converted from analog to digital form and normalized. From the normalized digitized amplitude responses and the average normalized digitized amplitude response of each cell, at a given origin position there is derived the standard deviation value for each cell. From the average normalized amplitude responses at a number of origin positions, the slope of the average amplitude response of each cell is calculated. From the ratio of the slope and deviation value, a weighting factor for uncertainty of or certainty of the response of each cell at each origin position is also calculated. The origin position with respect to each cell is then determined as being either to the left or to the right of that cell. The weighting factor, a representation of the location of each origin position, and normalized amplitude response for each cell for each position is stored in either a right or a left table associated with each cell. The stored representation of the location of each origin position may include simply the origin position (e.g. the distance to the origin position from some reference) or the product of the origin position and a weighting factor for that origin position. In the position determination or position analysis mode, the amplitude response of each cell is sampled in response to a radiant emission impinging on an unknown position on the multicell detector. These responses are converted from analog to digital form and normalized, as previously. The normalized, digitized amplitude responses of all cells are then compared to determine the two cells having the greatest amplitude response as a result of the emission event. It is then determined as to whether the cell with the greatest amplitude response is to the right or to the left of the cell with the second greatest amplitude response. The right table reference lookup is designated for all cells to the left of the cell with the greatest amplitude and the left table reference table lookup for the remainder of the cells when the cell with the greatest amplitude is to thè right of the cell with the second greatest amplitude; and the converse is true when the cell with the greatest amplitude is to the left of the one with the second greatest amplitude. The weighting factors derived from all the cells are summed, as are the representations of the locations of the origin positions derived from all of the cells. The sum of the respresentation of the origin positions is divided by the sum of the weighting factors to determine the position of impingement of the radiant emission on the multi-cell detector.

In preferred embodiments the cells of the multicell detector may be arranged in a two-dimensional array, and the function of the emission origin position, weighting factor and amplitude response for each origin position for each cell is stored in right and left tables for each dimension.

In further calibration in the two-dimensional approach, a second directing of radiant emission is made to the two-dimensional multicell detector from a number of known origin positions in each dimension, the position of impingement of the radiation emission on the detector is determined for each dimension and stored, correlated with the known origin position in each dimension in a transformation table. In two-dimensional position analysis, the same technique is used to determine the position of impingement of the emission on the detector in each dimension and then reference is made to the transformation table to determine the corresponding actual position of the impingement of the radial emission on the detector.

DISCLOSURE OF PREFERRED EMBODIMENTS

Other objects, features and advantages will occur from the following description of a preferred embodiment and the accompanying drawings, in which.

Figure 1:
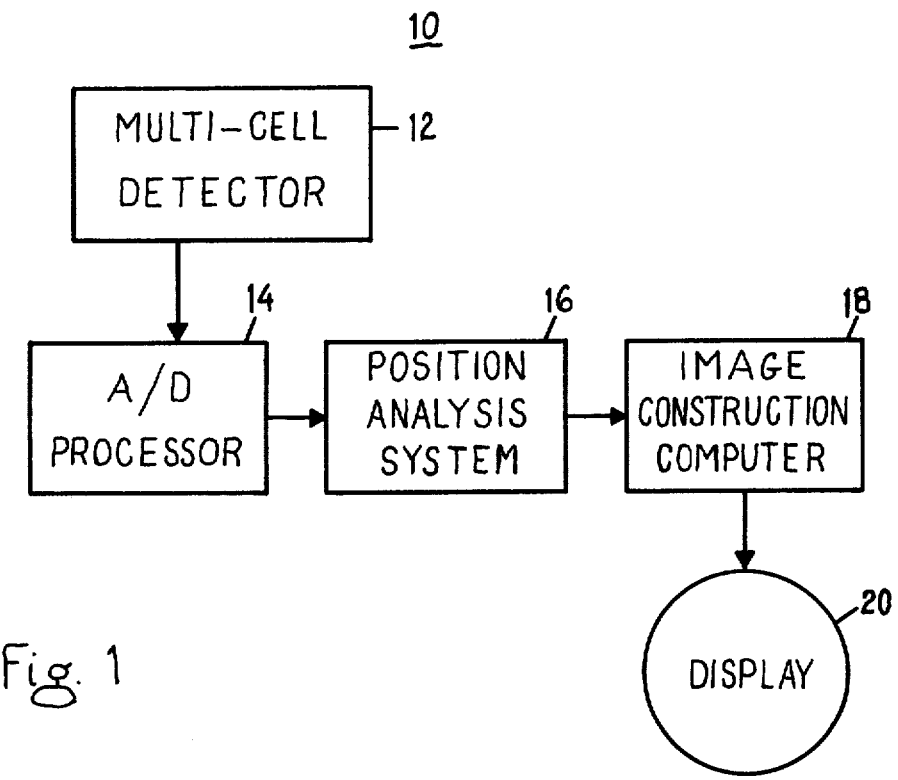
FIG. 1 is a block diagram of a radionuclide emission camera system.

There is shown in FIG. 1 radionuclide emission camera system 10 according to this invention including multi-cell detector 12, analog-digital processor 14, position analysis system 16, image construction computer 18, and display 20. The radionuclide emission event is sensed by multi-cell detector 12, which delivers an analog signal representative thereof to A to D processor 14. The digital output is submitted to position analysis system 16 according to this invention, which determines the position of the trajectory of the radiant emission, typically a gamma ray. With the position determined for each of the events, any one of a well-known number of processes can be applied to the position information by image construction computer 18 to construct the total image from a number of emission events. The image is then displayed on a conventional display 20. As more fully explained in the parent application, the image construction computer 18 receives position analysis information from multi-cell detector 12.

Figure 2:
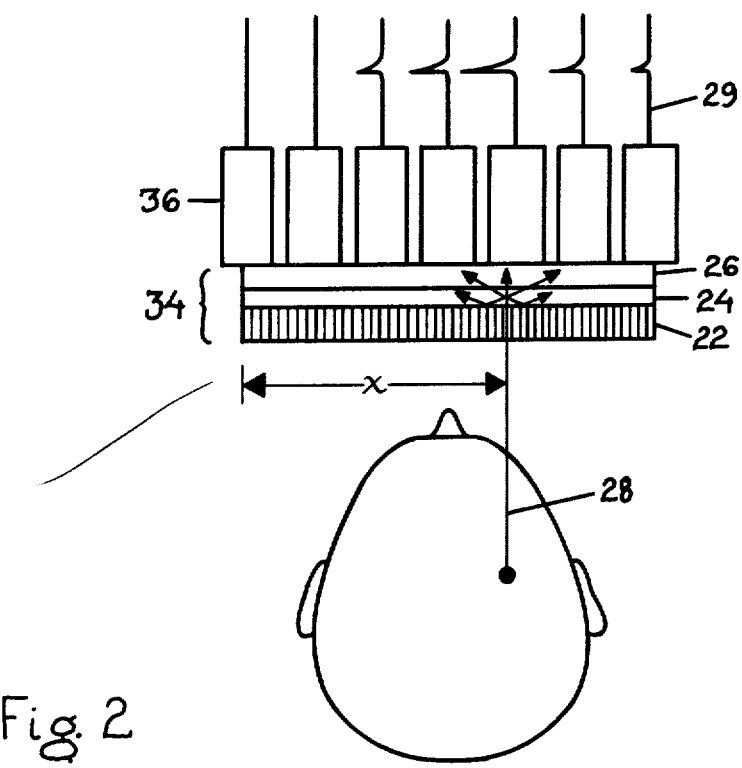
FIG. 2 is a more detailed view of the radionuclide multi-cell detector shown in FIG. 1.

Multi-cell detector 12 consists of a scintillation unit 34, FIG. 2, and photomultipliers 36. Scintillation unit 34 includes a collimator 22, scintillator 24, and light pipe 26. A gamma ray 28 emitted from a spot containing a radio-pharmaceutical in the head of a patient passes through collimator 22, and strikes scintillation layer 24, producing light rays that are transmitted through light pipe 26 to photomultipliers 36, which produce a number of electronic pulses 29 of varying amplitudes in response to the intensity of the light sensed.

Figure 3:
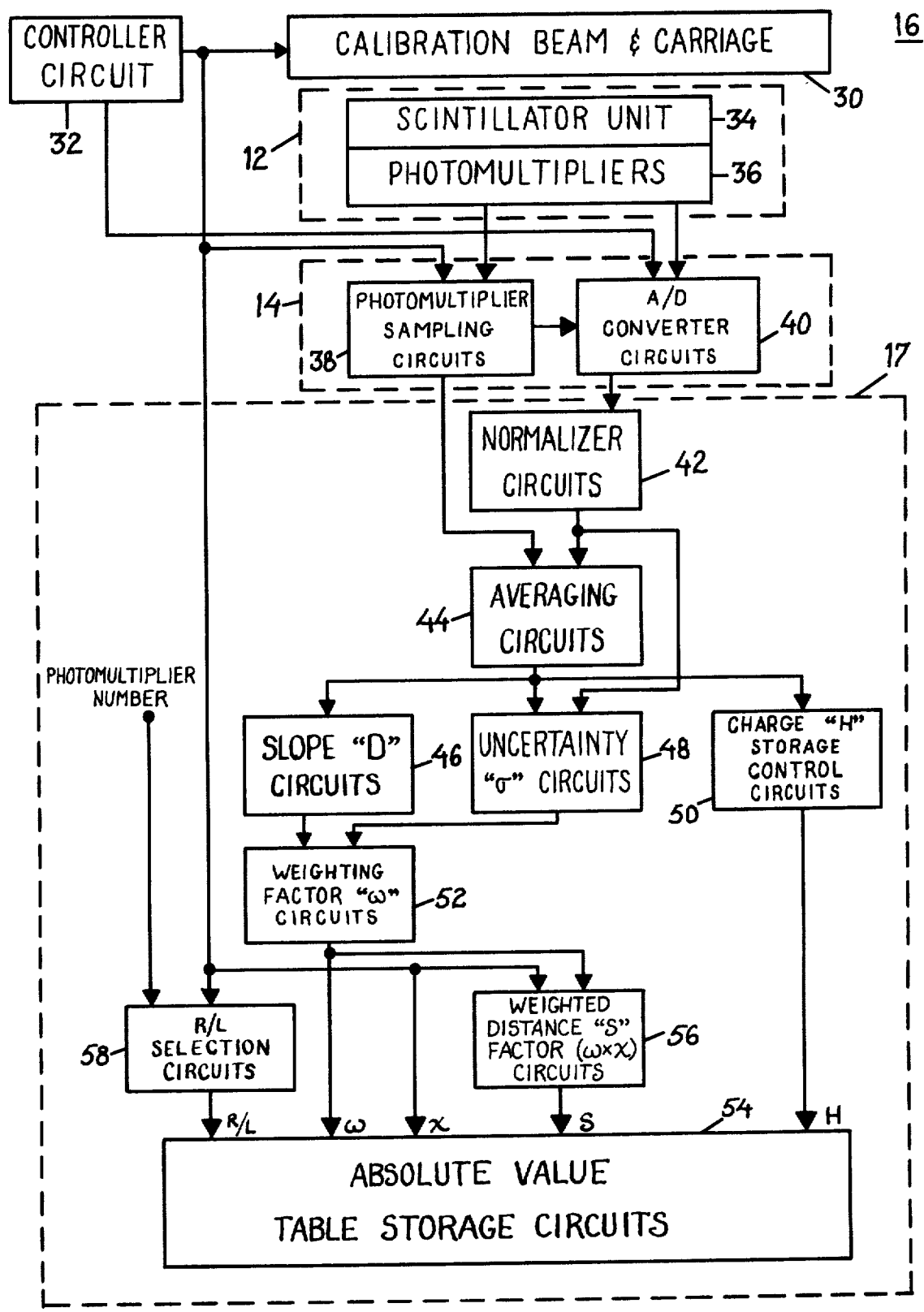
FIG. 3 is a more detailed block diagram of a calibration unit including a multi-cell detector, A to D processor, and position analysis system according to this invention.

A means of calibrating the position analysis system 16 according to this system includes a calibration gamma ray beam and carriage 30, FIG. 3, and a controller circuit 32 for moving the beam discretely through a succession of positions of known origin, origin positions, to direct radiant emissions to scintillator unit 34. Each scintillation is sensed from scintillator unit 34 by photomultipliers 36, which are sampled by photomultiplier sampling circuits 38. The analog output from the photomultipliers is directed by sampling circuits 38 to A to D converter circuits 40, where they are transformed to digital signals. The amplitude response of each of the photomultipliers 36 is then provided in digital form by A/D converter circuits 40 to normalizer circuits 42. Calibration unit 17 includes averaging circuits 44 which cause a number of samples to be taken from each photomultiplier cell at each origin position of the calibration beam and carriage 30. The averaged normalized output of these amplitude responses H is then submitted to slope-determining circuits 46, uncertainty circuits 48, and charge storage control circuits 50. Weighting factor circuits 52 determine the weighting factor $\omega$ from the slope and uncertainty signals from circuits 46 and 48. The weighting factor $\omega$ is stored directly in table storage circuits 54. A function e.g. representation of the location of the origin position is also stored in storage circuits 54. That function may include simply origin position information X from controller circuit 32 regarding the position of origin of the calibration beam 30, or the product S of the origin position X and weighting factor $\omega$ provided by weighted distance "S" factor circuits 56. Charge storage control circuits 50 act to enable storage circuits 54 to store the charge signal H in conjunction with the weighting factor $\omega$ and either one or both of the origin positions X or S. Whether the storage occurs in a right table or a left table depends upon the position of the scintillation event with respect to the photomultipliers. Right-left selection circuits 58 compare the real X position information from controller circuit 32 with the photomultiplier position number. If for any given photomultiplier the scintillation occurs to the left of that photomultiplier, then the information in table storage circuits 54 is directed to a left table; whereas if the scintillation occurs to the right, then the information will be stored in a right table.

Figure 4:
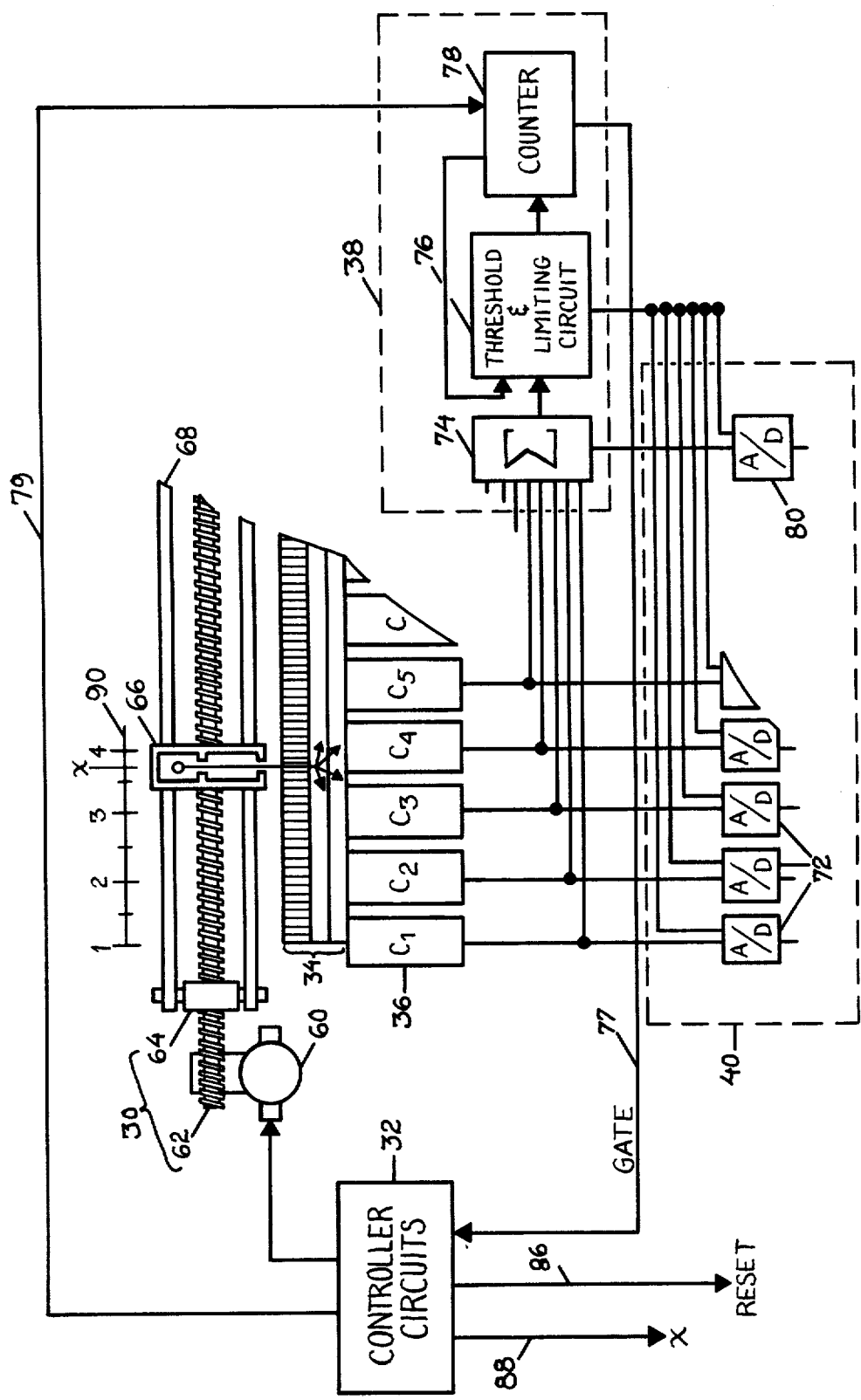
FIG. 4 is a more detailed description of the controller circuit, calibration beam and carriage, scintillating unit, photomultipliers, photomultiplier sampling circuits, and A to D converter circuits of FIG. 3.

Calibration beam and carriage 30 includes a drive motor 60, FIG. 4, which rotates a worm gear 62 in journal 64 to drive housing 66 along runners 68. Photomultipliers 36 include a number of individual photomultiplier cells $C_1$, $C_2$, $C_3$, etc. At each position the scintillation event is sensed through scintillator unit 34 by each of photomultipliers 36. The output of each photomultiplier cell 36 is directed to a separate A to D converter 72 and also to a summing circuit 74 in sampling circuits 38. If the sum of the amplitude responses of all the photomultipliers as submitted to the threshold and limiting circuit 76 is above the threshold level but below a limiting level, a signal is put out to counter 78 as well as to each of A to D converters 72 and to A to D converter 80. Upon receipt of these signals, A to D converters 72 and 80 convert from analog to digital form, and pass on for further processing signals provided at their input. Each signal delivered from threshold limiting circuit 76 to counter 78 registers that one scintillation event occurring in one position in the X direction has been sensed by photomultiplier cells 36. Another scintillation event occurs, the same cycle occurs again, and counter 78 registers another event. When some predetermined number of events occurring at that origin position, for example 1000, has been registered in counter 78, a signal is dispatched on line 77 to controller circuit 32, which then steps housing 66 to the next incremental X origin position. When this has been accomplished, a signal on line 79 from controller circuit 32 resets counter 78 and a number of scintillation events will be sensed at this position. Controller circuit 32 provides reset signal on line 86 and an indication of its X position on line 88 for submission to other parts of the system. The travel of housing 66 in the X direction is defined in terms of the center axis of each of the photomultiplier tubes; as indicated by the scale 90, the center of photomultiplier tube $C_1$ corresponds to the X position equal to one tube unit, whereas the center of photomultiplier tube $C_2$ and $C_3$ center axes correspond to the X positions 2, 3, units and so on.

Figure 5:
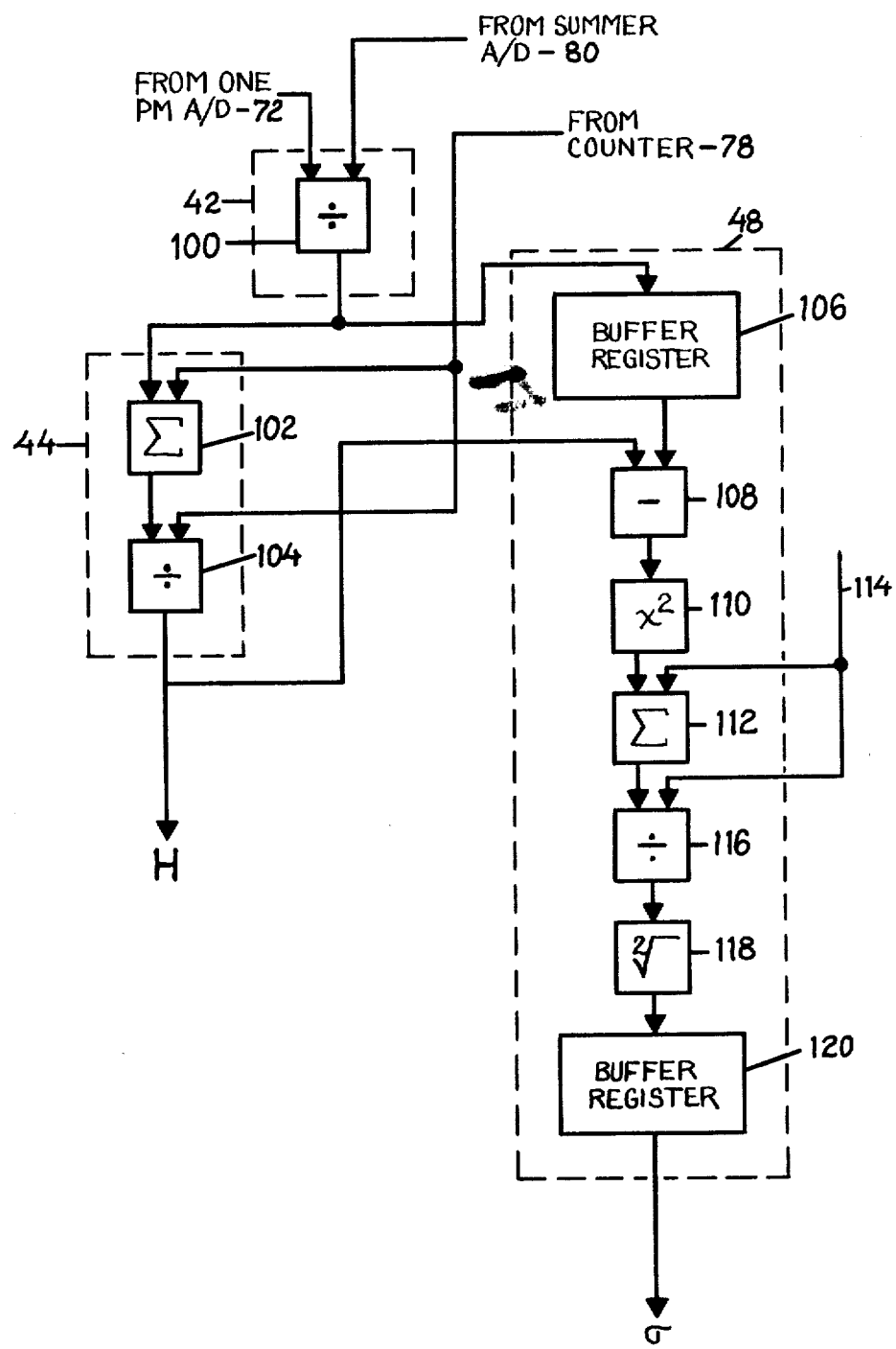
FIG. 5 is a more detailed block diagram of the normalizer circuits, averaging circuits, and uncertainty circuits of FIG. 3.

Normalizer circuits 42 include for each photomultiplier cell a divider 100, FIG. 5, which divides the A to D output for that photomultiplier cell by the output from the A to D responsive to the summation circuit 74. Averaging circuits 44 include summing circuit 102 which sums each normalized output during an entire cycle of counter 78 and then divides that sum by the number of events that were sampled, i.e. the number of cycles registered in counter 78, in divider circuit 104 to determine the average normalized value. This average normalized value is submitted to the uncertainty circuit 48, which for each photomultiplier cell includes a buffer register 106 which receives each normalized signal and stores it, awaiting the occurrence of the average normalized signal value from divider circuit 104. When this occurs, the difference is obtained by subtractor circuit 108 and squared in circuit 110. The square of the difference is summed in circuit 112 a number of times equal to the total count in counter 78 as indicated on line 114. This sum of the squares of the differences is then divided in circuit 116 by the number of events counted by counter 78 as supplied on line 114, and then the square root of that is taken in circuit 118 and stored as the standard deviation factor, $\sigma$, in buffer register 120.

Figure 6:
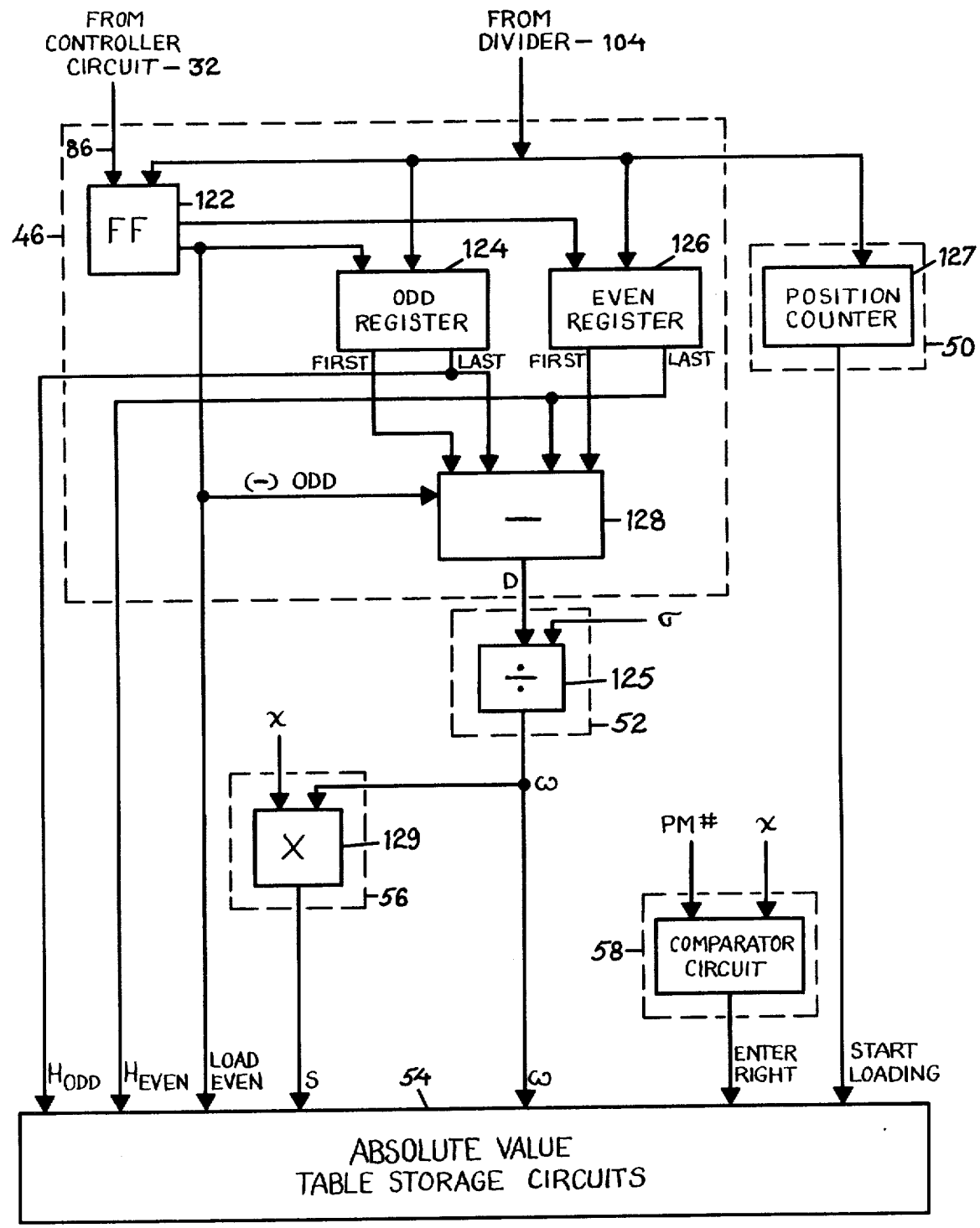
FIG. 6 is a more detailed block diagram of the slope-determining circuits, charge storage control circuits, weighting factor circuits, weighted distance factor circuits, and right-left selection circuits of FIG. 3.

Slope-determining circuits 46, FIG. 6, include for each photomultiplier cell a flip-flop 122 which is reset by a signal from controller circuits 32 on line 86 and counts one count for each origin position division. Flip-flop 122 gates the information from the average normalized signal from divider 104 either into odd register 124 or even register 126; that is, at the first, third, seventh, etc., X origin position divisions, odd register 124 receives the average normalized input from divider 104, while at the even X origin position divisions 2, 4, 6, 8, etc., even register 126 receives the information. Each of the registers stores only the last two signals that it has received. Subtractor circuit 128 subtracts the first and last signals, or last two signals, in either one or the other of registers 124 and 126 to obtain the slope of the amplitude response of that photomultiplier at the point between those two signals. Thus if odd register 124 is currently storing data from the first and third X origin positions the subtraction of those two amplitudes by circuit 128 results in the slope of the amplitude response of that photomultiplier cell at $X=2$ origin position. The signal from flip-flop 122, which has enabled odd register 124 to accept the last signal from divider 104, also simultaneously enables subtractor 128 to subtract the odd inputs and instructs table storage circuit 54 to load the amplitude response $H_{even}$ from the even register. When flip-flop 122 directs the latest input from divider 104 to be directed to even register 126, subtractor 128 in the absence of the subtracted odd signal then substracts the inputs from even register 126; in the absence of a load even signal the amplitude response H is loaded in table storage circuit 54. Since insufficient information is contained in the odd and even registers 124 and 126 until at least three X positions have been achieved, charge storage control circuits 50 include an X position counter 127, used to enable loading of table storage circuit 54 to begin only after X position counter 127 has reached a count of three. In that case, for example, where there have been three X positions achieved, odd register 124 has the information from positions 1 and 3, while even register 126 contains the information from position 2. Since the last bit of information was an odd bit, flip-flop 122 enables odd register 124 to accept the third and last parcel of information, and also enables subtractor 128 to subtract the first and last parcels of information from each other to provide the slope D. Simultaneously, the $H_{even}$ signal is loaded by virtue of the load even signal provided by flip-flop 122. The reciprocal of the uncertainty of the position of X or $\omega$, as a weighting factor, may be determined from the ratio of the slope and deviation, e.g. by dividing the slope calculated by circuit 128 by the standard deviation calculated by circuit 48 in divider circuit 125 of circuit 52. As subsequently explained, the determined position of impingement of the emission on the detector $\overline{X}$ is equal to the summation of $\omega$ divided into the sum of the products of $\omega$ and $X = S$. S may be calculated by multiplying the origin position X from controller circuit 32 by weighting factor $\omega$ in multiplier circuit 129 of circuit 56.

Figures 7, 8:
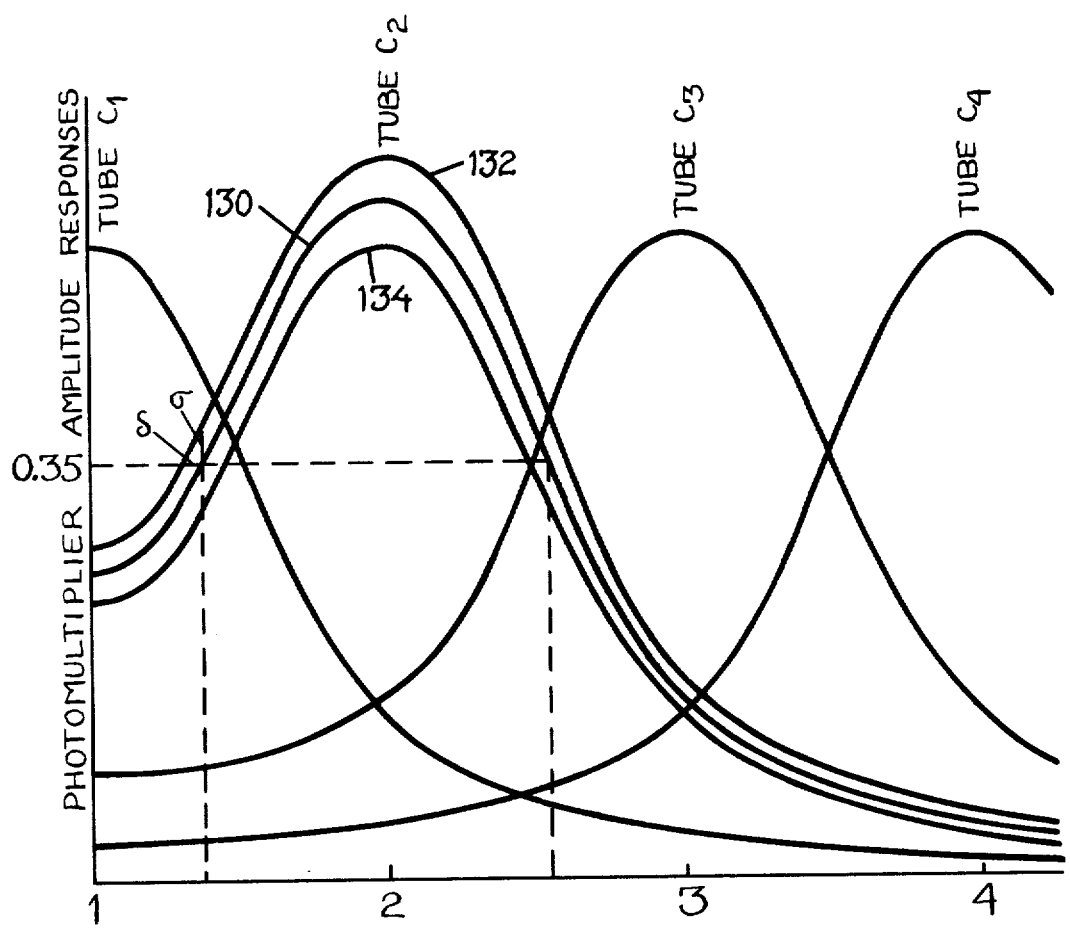
FIG. 7 is an illustrative example of a part of a right and a left table for a single photomultiplier tube which is stored in the table storage circuits of FIG. 3, correlating the average amplitude response, origin position, weighting factor, and representation of the origin position.
FIG. 8 is a graph illustrating the amplitude response of a number of photomultiplier tubes with respect to the location of the scintillation event with respect to those tubes.

Typical absolute values i.e. the value independent of sign stored for a typical cell through a traverse in the X direction of the calibration beam and carriage is shown in FIG. 7, where there is shown for photomultiplier tube $C_2$ at the 2.0 position, the construction of the left and right tables which are stored in table storage circuits 54 as a result of the calibration. There each amplitude response H in the left-most column has a corresponding position X, weighting factor $\omega$, and weighting distance factor S. Both S and X need not be stored, but some function of X is stored: either $S = (\omega \cdot X)$, in which case S is all ready for use in the position analysis mode, or simply X, which must then later be multiplied by $\omega$ for use in the analysis mode. Typically X is not stored.

Further, in FIG. 7, the difference between a scintillation event occurring to the left of tube $C_2$ and to the right of tube $C_2$ is noted. For example, for an amplitude response H of 0.35, if the scintillation event occurs to the left, as at position 1.38, the weighting coefficient is 16.78 and the S factor is 23.16; whereas if the scintillation event occurs to the right at position 2.54, the weighting coefficient is 22.44 and the S factor is 57.00. The response of the tube $C_2$ and surrounding tubes may be better understood from the table of FIG. 7 in conjunction with the graph of FIG. 8, wherein the X position is plotted along the abscissa and the photomultiplier amplitude response is plotted along the ordinate for the first four photomultipliers of a linear array. There it can be seen, for example, that for tube $C_2$ the 2.55 point and the 1.38 point in the X position both correspond to a 0.35 amplitude response. The characteristic 130 of tube $C_2$ is surrounded by the upper and lower envelopes 132 and 134, respectively, which are the uncertainty limits of the average normalized values. $\sigma$ is the uncertainty in amplitude response, while $\omega$ is the uncertainty in the X position response.

In subsequent figures, like parts have been given like numbers and similar parts like numbers accompanied by a lower case letter.

Figure 9:
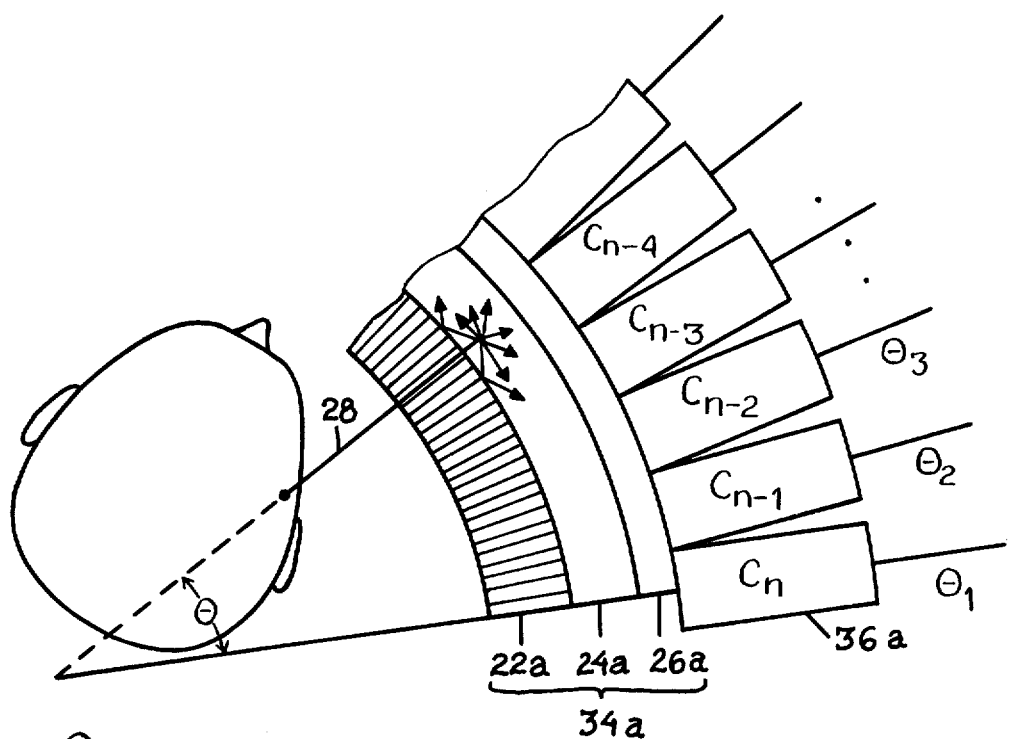
FIG. 9 shows a transaxial radionuclide emission camera multi-cell detector similar to that of FIG. 2 with arcuate geometry.

Although the invention thus far has been described with respect to a one-dimensional linear or flat geometry, this is not a necessary limitation of the invention, for as shown in FIG. 9, photomultipliers 36 may be disposed in a circular arc, in which case the X dimension is referred to as the $\theta$ dimension, and the response of these phototubes is slightly changed due to the curved geometry.

Figure 10:
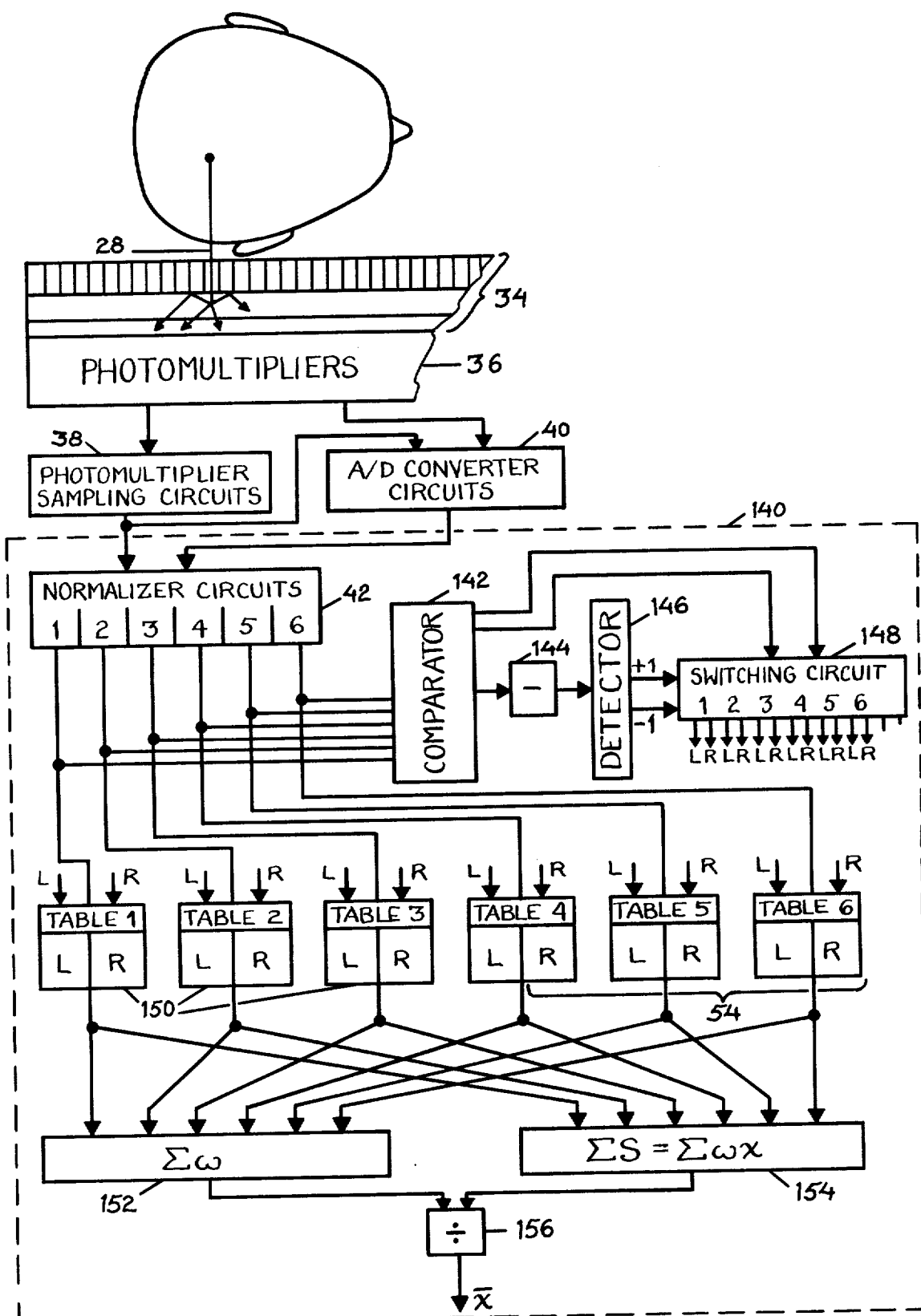
FIG. 10 is a position analysis unit for determining the position of an unknown scintillation event.

For position analysis determination, a position analysis unit 140, FIG. 10, uses photomultipliers 36 and scintillation unit 34, which receive a gamma ray 28 emitted from an area of a patient's head. The signals from each of the photomultipliers 36 are processed in photomultiplier sampling circuits 38, A to D converter circuits 40, and normalizer circuits 42.

For a particular scintillation, the outputs from normalizer circuits 42 of all photomultipliers are compared in comparator 142, where the two having the greatest amplitude response are selected. The X origin position of each of those two photocells determined by scale 90, FIG. 4, is then identified, and the X position of the one of the two photocells having the second greatest amplitude is subtracted from the X origin position of the photocell having the greatest amplitude. If the result is a $+1$, detector 146 causes switching circuit 148 to enable right table lookup for all photomultiplier cells lower in position number than the photomultiplier cell of greatest amplitude and enable left table lookup for the photomultiplier cells to its right. When detector 146 detects a $-1$ difference, switching circuit 148 operates conversely. Each photomultiplier cell thus has associated with it a readout from one of tables 150 in storage 54, either the right table or the left table, so that a weighting factor $\omega$ for each photomultiplier cell is accumulated, and they are all summed by summing circuit 152. Similarly, summing circuit 154 accumulates and sums all of the S factors, one from each table for each photomultiplier cell, or if the S factor is not stored, then its constituents $\omega$ and the X position are retrieved and their product S is formed. The summation of all the S factors is divided by the summation of all the $\omega$ factors in divider 156 to provide the determined position $\overline{X}$ of impingement of the radiant emission on the detector. The division of the sums may be accomplished by summing the values for all cells or by independently summing and dividing those values for two or more sets or groups, such as, for example, grouping all the left cell responses for summing and division in one group and all the right in another and then adding the results and averaging.

Figure 11:
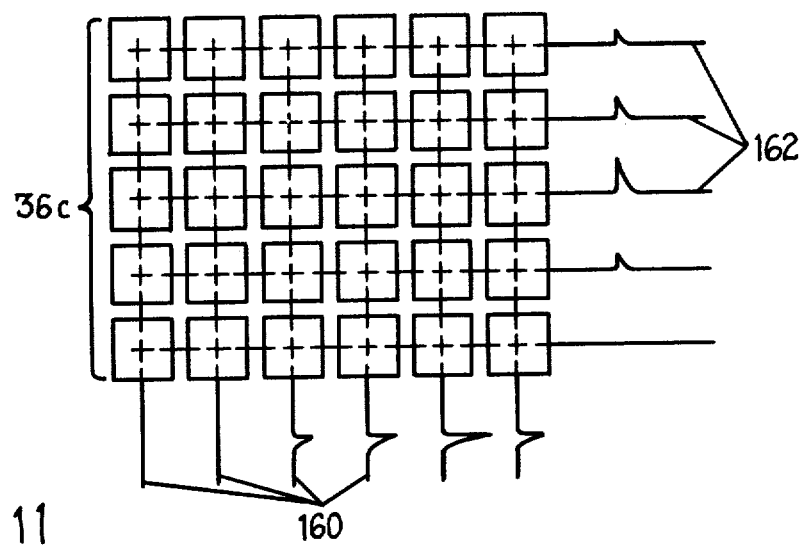
FIG. 11 is a schematic diagram of a two-dimensional array of cells in a multi-cell detector.

Although thus far the invention has been described with respect to a one-dimensional linear or arcuate detector, this is not a necessary limitation of the invention, for as shown in FIG. 11, two-dimensional arrays of photomultipliers 36c may also be used. In that case the position $\overline{X}$ of impingement of an emission is determined from signals on lines 160 from all of the photomultiplier cells in each column, and the second dimension, or the position $\overline{Y}$ of impingement of an emission is determined from signals on lines 162 from all of the photomultiplier cells in each of the corresponding rows.

Figure 12:
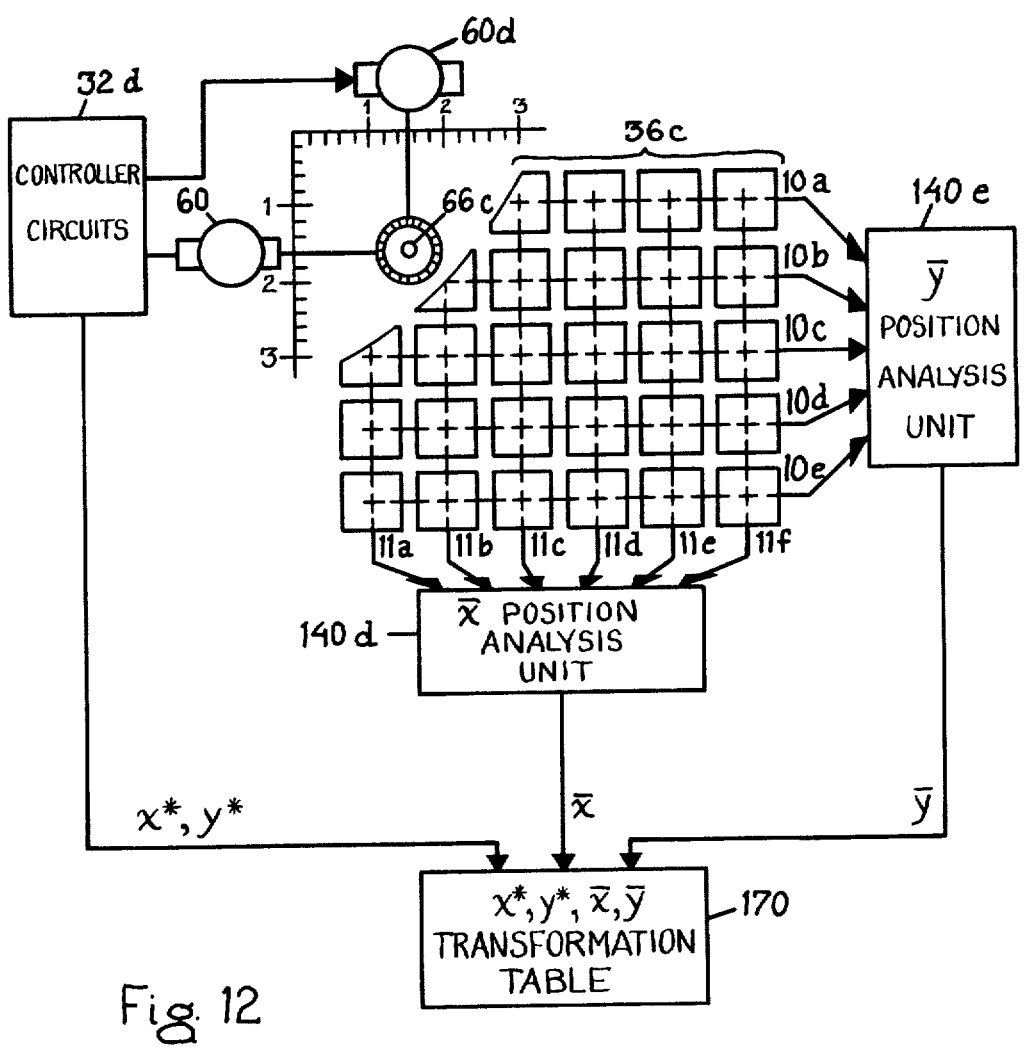
FIG. 12 is a diagram of the two-dimensional array of FIG. 11 and a block diagram of a system for constructing a transformation table.

Calibration of two-dimensional matrix 36c is accomplished similarly to that for one-dimensional detectors, except that controller circuits 32d, FIG. 12, drives two motors, an X motor 60 and a Y motor 60d, which move housing 66c in two dimensions. Further, there is an X position analysis unit 140d and a Y position analysis unit 140e, which determine the $\overline{X}$ position of impingement of an emission and the $\overline{Y}$ position of impingement of an emission, and provide them to transformation table 170, in conjunction with simultaneous indications from controller circuits 32d of the actual X* and Y* positions of the origin of the emission. In this way the dependence of the X responses on the Y position and the Y responses on the X position may be accounted for. Thus, for each determined $\overline{X}$ and $\overline{Y}$ position from position analysis unit 140d and 140e inserted in transformation table 170, there is an X*, Y* actual position from controller circuits 32d which is stored in conjunction with it. Thus any non-linearity, non-isotropicity, or any other non-uniformity in the performance of matrix 36c is accounted for by constructing transformation table 170, wherein each determined value of $\overline{X}$ and $\overline{Y}$ is correlated with the actual values of X* and Y* of the gamma ray at that point.

Although only two axes X, Y, have been shown and the X, Y axes have been shown orthogonal to each other, this is not a necessary limitation of the invention: there may be more than two axes at other orientations. For example, for axes with a hexagonal array of photocells, three axes at 60° may be used which are converted to $\overline{X}$, $\overline{Y}$.

Figure 13:
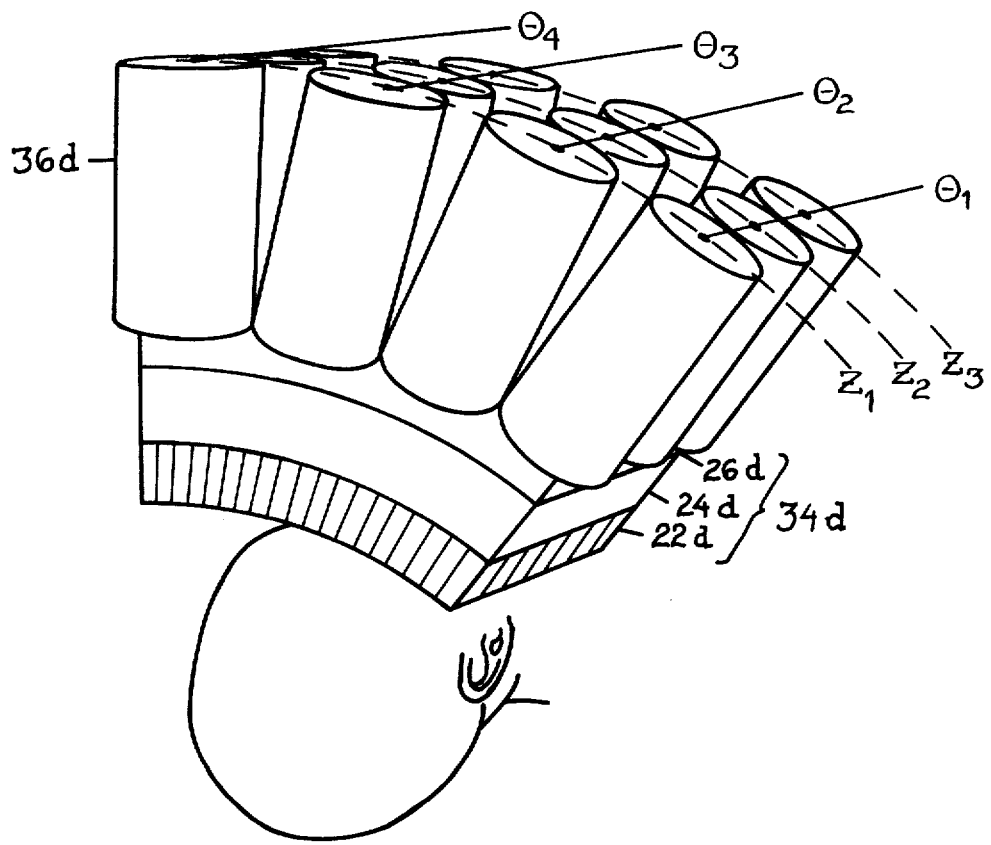
FIG. 13 is a partial axonometric view of a multi-cell detector similar to that of FIG. 9 having cylindrical geometry.

Although thus far the two-dimensional discussion has shown only relatively planar detectors, this is not a necessary limitation of the invention, as can be seen in FIG. 13, where a camera having cylindrical geometry is shown.

Figure 14:
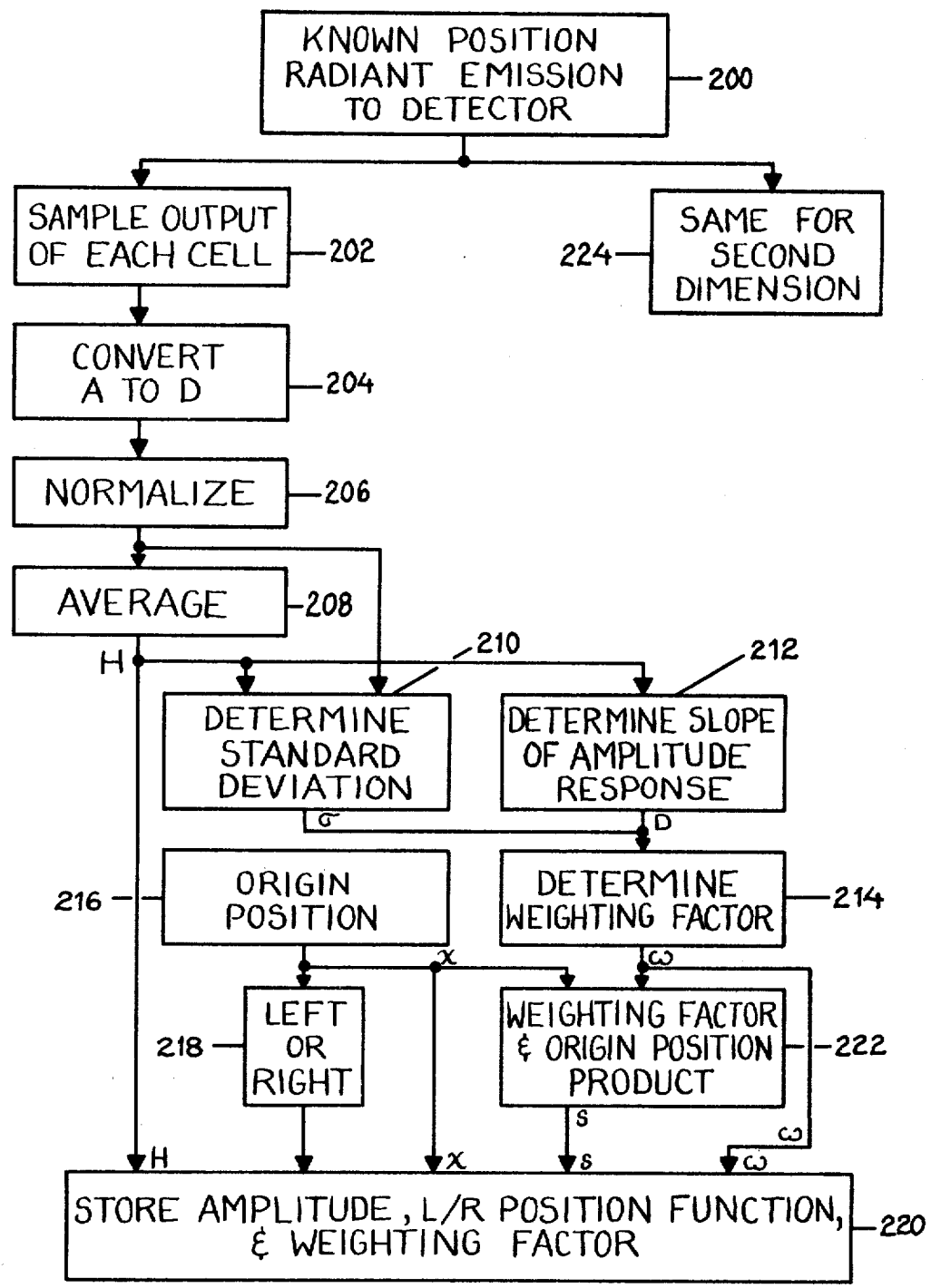
FIG. 14 is a schematic block diagram of a method of calibrating a radionuclide emission camera system according to this invention.

The method according to this invention may be effected with the apparatus shown or programmed microprocessors or computers and involves effecting a radiant emission to each detector 200, FIG. 14. The output of each cell is sampled, 202, and converted from analog to digital form, 204. Each signal is normalized and the average of a number of those normalized digitized amplitude responses H is made, 208. The normalized value and the average normalized value are used to determine the standard deviation value 210, $\sigma$, while the average value of the normalized, digitized responses are used to determine the slope of the amplitude response, 212. The slope and the standard deviation are combined to determine a weighting factor 214, $\omega$.

The origin position X, 216, is determined as is the left or right table store 218. The weighting factor $\omega$ may be multiplied with the origin position X, 222, to obtain S. The values of H, $\omega$, and a function of the origin position X, either S or X, are stored 220 in either the left or right table of each tube. For two-dimensional detectors the same method is effected for the second dimension, 224.

Figure 15:
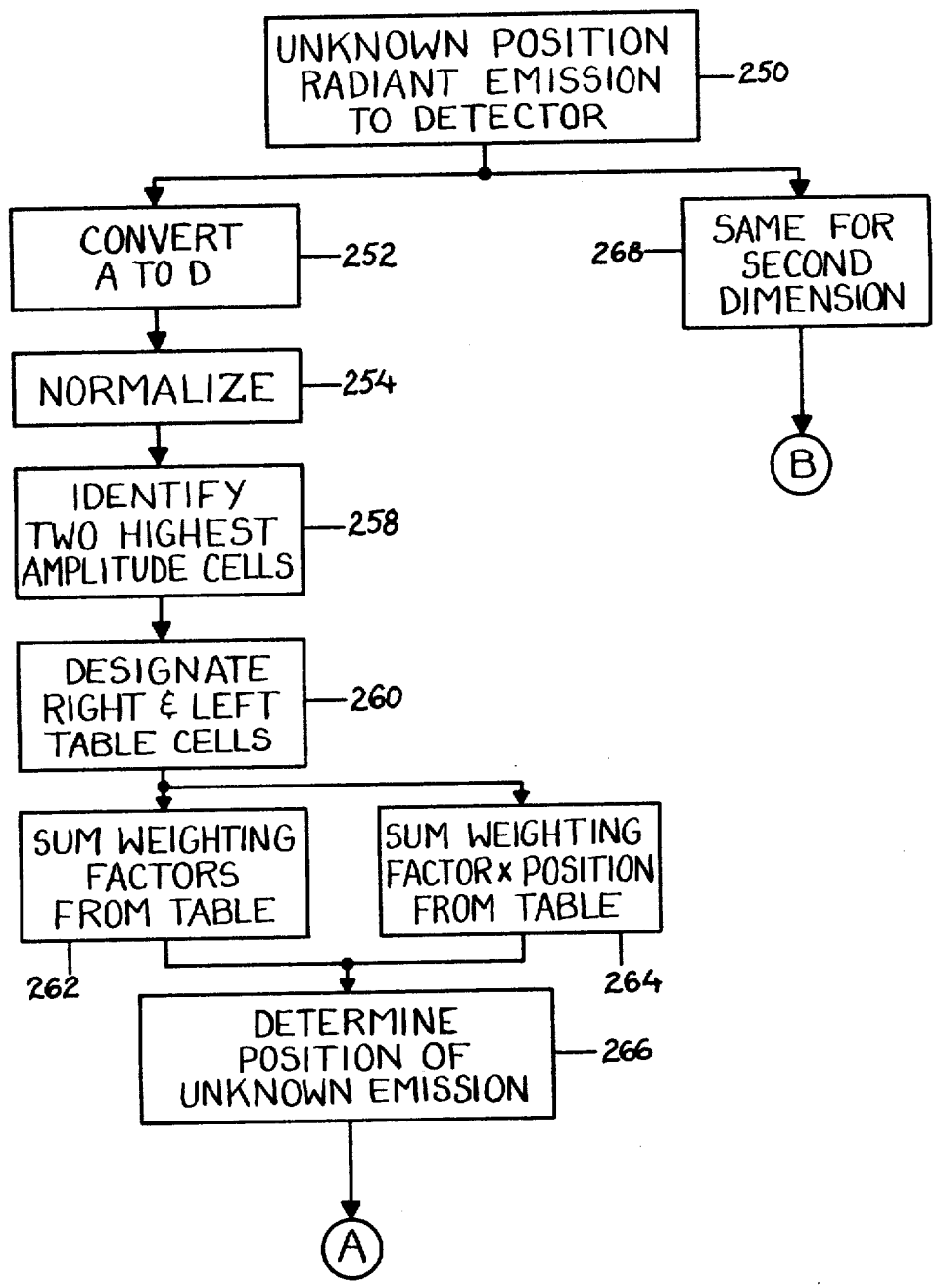
FIG. 15 is a schematic block diagram of a method of position analysis according to this invention.

Position analysis according to this method begins with a radiant emission impinging on a detector at an unknown position 250, FIG. 15. The output of each of the photomultipliers is converted from analog to digital form, 252, and normalized, 254. The two photomultiplier cells having the highest amplitudes are identified, 258, and a determination is made as to whether the photocell having the second highest amplitude is to the left or to the right of the photomultiplier cells whose amplitude response is the greatest. In dependence upon this, either the right or the left table lookup is identified, 260, for the photomultiplier cells to the left and to the right of that having the greatest amplitude. Then the weighting factors from one of the left and right tables for each of the photocells is summed, 262, as is the product of the weighting factor and emission origin position, 264. The latter is then divided by the former to determine, 266, the unknown emission impingement position $\overline{X}$. For two-dimensional detectors, the same technique is used for the second dimension, 268.

Figure 16:
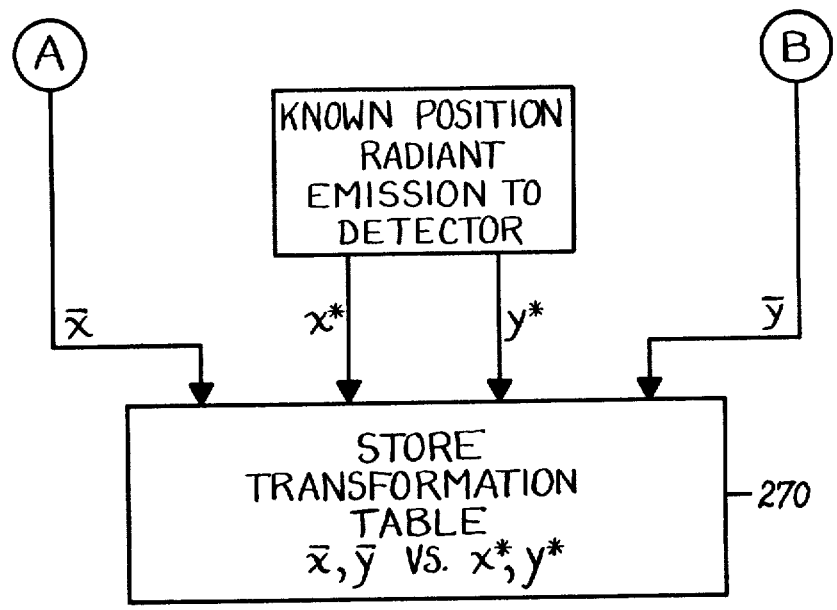
FIG. 16 is a schematic block diagram showing the establishment of a transformation table in further calibration according to this invention.
Figure 17:
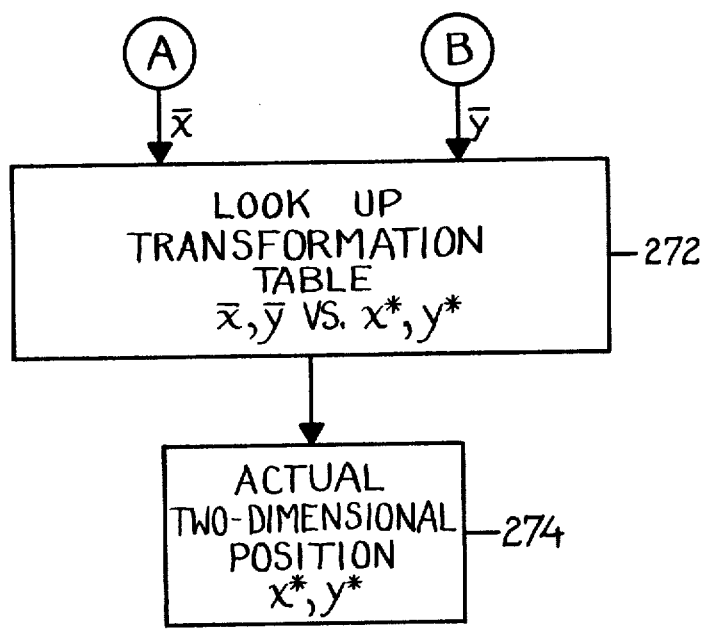
FIG. 17 is a schematic block diagram showing the use of a transformation table in two-dimensional position analysis according to this invention.

Also, for use of two-dimension detectors the determined $\overline{X}$ position and determined $\overline{Y}$ position are stored in a transformation table 270, FIG. 16, correlated with the known origin positions X*, Y*, of a radiant emission to the detectors, so that the actual position of an emission is correlated with the determined position of that emission striking the detector. When position analysis is performed, the determined $\overline{X}$ and $\overline{Y}$ values are simply submitted to the transformation table 272, FIG. 17, to determine the X*, Y* actual values, 274.

Other embodiments will occur to those skilled in the art and are within the following claims:

What is claimed is:

1. A method of digital calibration and position analysis of impingement of a radiant emission on a multicell detector comprising:
   directing radiant emissions to a number of known origin positions at said multicell detector; and for each origin position;
   sampling the amplitude response of each cell a number of times;
   converting form analog to digital form the amplitude response of each cell;
   normalizing the digitized amplitude response of each cell;
   averaging the normalized digital amplitude response of each cell;
   determining from the average normalized digitized amplitude response and normalized digitized amplitude response of each cell, the standard deviation value for each cell and the slope of the amplitude response of each cell;
   determining from the ratio of the slope and deviation value a weighting factor, representing the uncertainty of the origin position, for the response of each cell at each origin position;
   determining with respect to each cell whether the origin position is to the left or right of it; and
   storing in one of a right and a left table for each cell a representation of the location of each origin position of emission, the weighting factor, and normalized amplitude response for each cell for each origin position.

2. The digital calibration and position analysis method of claim 1 in which the representation of the location of each origin position includes the origin position and a weighting factor.

3. The digital calibration and position analysis method of claim 1 further including sampling the amplitude response of each cell in response to a radiant emission impinging on an unknown position on the multicell detector; converting from analog to digital form the response of each cell; normalizing the digital output of each cell; comparing the normalized digitized amplitude response of each cell to determine the two of greatest amplitude; determining whether the cell with the greatest amplitude response is to the right or to the left of the one with the second greatest amplitude response; designating right table reference for all cells to the left of the cell with the greatest amplitude and left table reference for the remaining cells when the cell with the greatest amplitude is to the right of the cell with the second greatest amplitude and designating left table reference for all cells to the right of the cell with the greatest amplitude and right table reference for all the remaining cells when the cell with the greatest amplitude is to the left of the cell with the second greatest amplitude; independently summing the weighting factor and a representation of the location of each origin position for each cell; and dividing the sum of the representation of the location of each origin position by the sum of the weighting factors in at least one group to determine the position of impingement of the radiant emission on the detector.

4. The digital calibration and position analysis method of claim 1 in which the cells of said multicell detector are arranged in a two-dimensional array and the weighting factor and the representation of the location of the origin position of each emission and amplitude response for each position is determined and stored in right or left table for each dimension.

5. The digital calibration and position analysis method of claim 4 in which a second directing of radiant emissions to said multicell detector is made from a number of known origin positions in each dimension and the position of impingement of the radiation emission on the detector is determined for each dimension and is stored correlated with the known origin position in each dimension in a transformation table.

6. The digital calibration and position analysis method of claim 5 further including, for each dimension, sampling the amplitude response of each cell in response to a radiant emission impinging on an unknown position on the multicell detector; converting from analog to digital form the response of each cell; normalizing the digital output of each cell; comparing the normalized digitized amplitude response of the cells to determine the two of greatest amplitude; determining whether the cell with the greatest amplitude response is to the right or to the left of the one with the second greatest amplitude response; designating right table reference for all cells to the left of the cell with the greatest amplitude and left table reference for the remaining cells when the cell with the greatest amplitude is to the right of the cell with the second greatest amplitude and designating left table reference for all cells to the right of the cell with the greatest amplitude and right table reference for all the remaining cells when the cell with the greatest amplitude is to the left of the cell with the second greatest amplitude; independently summing the weighting factor and a representation of the location of each origin position for each cell; and dividing the sum of the representation of the location of each origin position of emission by the sum of the weighting factors in at least one group to determine the position of impingement of the radiant emission on the detector for each dimension; and searching the transformation table to find the actual position of impingement of the radiant emission on the detector from the determined position of impingement.

7. A system for digital calibration of the position of impingement of a radiant emission on a multicell detector comprising:
means for directing radiant emissions to said multicell detector from a number of known positions;
means for sampling the amplitude response of each cell a number of times at each position of the emission;
means for converting the analog amplitude response of each cell to a digital amplitude response;
means for normalizing the digital amplitude response of each cell;
means for averaging the normalized digital amplitude response of each cell;
means, responsive to said means for normalizing, and said means for averaging the normalized digital amplitude response, for determining the standard deviation value for each cell at its respective amplitude;
means, responsive to said means for normalizing, for determining the slope of the amplitude response of each cell at each emission position;
divider means, responsive to said means for determining slope and said means for determining standard deviation value, for calculating a weighting factor representing the uncertainty of the origin position for each cell at each emission origin position;
means, responsive to said means for directing radiant emissions, for indicating the origin position of the impinging radiant emission;
means, responsive to said means for indicating origin position, for establishing the relative direction of the impingement relative to each cell;
means, responsive to said means for establishing, for storing the amplitude response of each cell for each radiant emission origin position and the corresponding weighting factor and representation of the location of each origin position in one of two storage areas.

8. A system for digital calibration in each of two dimensions of the position of impingement of a radiant emission on a multicell two-dimensional array detector including a calibration unit associated with each dimension, each said calibration unit comprising:
means for directing radiant emissions to said multicell detector from a number of known positions;
means for sampling the amplitude response of each cell a number of times at each position of the emission;
means for converting the analog amplitude response of each cell to a digital amplitude response;
means for normalizing the digital amplitude response of each cell;
means for averaging the normalized digital amplitude response of each cell;
means, responsive to said means for normalizing, and said means for averaging the normalized digital amplitude response, for determining the standard deviation value for each cell at its respective amplitude;
means, responsive to said means for normalizing, for determining the slope of the amplitude response of each cell at each emission position;
divider means, responsive to said means for determining slope and said means for determining standard deviation value, for calculating a weighting factor representing the uncertainty of the origin position for each cell at each origin position;
means, responsive to said means for directing radiant emissions, for indicating the origin position of the impinging radiant emission;

means, responsive to said means for indicating origin position, for establishing the relative direction of the impingement relative to each cell;

means, responsive to said means for establishing, for storing the amplitude response of each cell for each radiant emission origin position and the corresponding weighting factor and representation of the location of each origin position in one of two storage areas.

9. The system of claim 8 further including means for directing radiant emissions to said detector to a number of known origin positions in each dimension; and means for storing each said origin position in each dimension with its correlated determined position established by said calibration units for forming a transformation table correlating actual and determined impingement positions in each dimension.

10. A digital system for position analysis of impingement of a radiant emission on a multicell detector comprising:

means for sampling the output of each cell to detect its output in response to a radiant emission impinging on an undefined position on the detector;

means for converting the analog output of each cell to a digital output;

means for normalizing the digital output of each cell;

means for comparing the normalized digital output of each cell to determine the two cells having greatest amplitude response;

means for determining whether the cell with the greatest amplitude response is to the left or the right of the one with the second greatest amplitude;

means for storing for each cell for each origin position of emission left and right tables, each table including a representation of the location of each origin position of emission, weighting fctor representing the uncertainty of the origin position, and normalized amplitude response;

switching means, responsive to the cell with the greatest amplitude being to the right of the cell with the second greatest amplitude, for enabling the right table for all cells to the left of the cell with the greatest amplitude and enabling left tables for the remaining cells; and responsive to the cell with the greatest amplitude being to the left of the cell with the second greatest amplitude, for enabling the left table for all cells to the right of the cell with the greatest amplitude and enabling right tables for the remaining cells;

means for summing independently from each enabled table of each cell the weighting factor and the representation of the location of the origin positions of emission; and means, responsive to said means for summing, for dividing said representation of the location of the origin position sum by said weighting factor sum in at least one group to establish the position of impingement of the radiant emission on the detector.

11. A digital system for determining in each dimension the position of impingement of a radiant emission on a multicell two-dimensional array detector including a position determining unit associated with each dimension, each unit comprising:

means for sampling the output of each cell to detect its output in response to a radiant emission impinging on an undefined position on the detector;

means for converting the analog output of each cell to a digital output;

means for normalizing the digital output of each cell;

means for comparing the normalized digital output of each cell to determine the two cells having the greatest amplitude response;

means for determining whether the cell with the greatest amplitude response is to the left or the right of the one with the second greatest amplitude;

means for storing for each cell for each origin position of emission left and right tables, each table including a representation of the location of each origin position of emission, weighting factor representing the uncertainty of the origin position, and normalized amplitude response;

switching means, responsive to the cell with the greatest amplitude being to the right of the cell with the second greatest amplitude, for enabling the right table for all cells to the left of the cell with the greatest amplitude and enabling left tables for the remaining cells; and responsive to the cell with the greatest amplitude being to the left of the cell with the second greatest amplitude, for enabling the left table for all cells to the right of the cell with the greatest amplitude and enabling right tables for the remaining cells;

means for summing independently from each enabled table of each cell the weighting factor and the representation of the location of the origin positions of emission;

means, responsive to said means for summing, for dividing said representation of the location of the origin position sum by said weighting factor sum in at least one group to establish the position of impingement of the radiant emission on the detector; and determining means for providing for each determined impingement position in each dimension a corresponding actual position in each dimension.

* * * * *